(12) United States Patent
Coudert et al.

(10) Patent No.: US 8,261,600 B2
(45) Date of Patent: Sep. 11, 2012

(54) METHOD FOR ANALYZING A SCRATCH TEST

(75) Inventors: Pierre-Jean Coudert, Brindas (FR); Bertrand Bellaton, Neuchatel (CH)

(73) Assignee: CSM Instruments SA, Peseux (CH)

( * ) Notice: Subject to any disclaimer, the term of this patent is extended or adjusted under 35 U.S.C. 154(b) by 849 days.

(21) Appl. No.: 12/324,237

(22) Filed: Nov. 26, 2008

(65) Prior Publication Data
US 2009/0145208 A1  Jun. 11, 2009

(30) Foreign Application Priority Data
Nov. 27, 2007 (EP) .................................. 07121669

(51) Int. Cl.
*G01N 3/46* (2006.01)
*G06K 9/00* (2006.01)
*G06K 15/00* (2006.01)

(52) U.S. Cl. ............................................. 73/81; 382/100
(58) Field of Classification Search .......... 73/81, 150 R, 73/150 A, 105; 348/142; 356/600, 614–615, 356/625, 628; 382/100, 106, 108, 141, 154
See application file for complete search history.

(56) References Cited

U.S. PATENT DOCUMENTS

| | | | |
|---|---|---|---|
| 4,463,600 A * | 8/1984 | Hobbs et al. ........................ | 73/81 |
| 4,627,096 A * | 12/1986 | Grattoni et al. .................. | 382/141 |
| 4,653,106 A * | 3/1987 | Yamatsuta et al. ............... | 382/141 |
| 4,945,490 A * | 7/1990 | Biddle et al. ....................... | 73/81 X |
| 5,866,807 A * | 2/1999 | Elings et al. ...................... | 73/105 |
| 6,996,264 B2 * | 2/2006 | Hauck et al. ...................... | 382/141 |
| 2002/0104371 A1 | 8/2002 | Gitis et al. | |
| 2004/0096093 A1 * | 5/2004 | Hauck et al. ...................... | 382/141 |
| 2005/0265593 A1 * | 12/2005 | Hauck et al. ...................... | 382/141 |
| 2006/0171579 A1 * | 8/2006 | Lee et al. ........................... | 382/141 |

FOREIGN PATENT DOCUMENTS

| | | | | | |
|---|---|---|---|---|---|
| GB | 2197463 A | * | 5/1988 | ............... | 348/E5.029 |
| JP | 57148233 A | * | 9/1982 | ............... | 73/82 |
| JP | 59216036 A | * | 12/1984 | | |
| JP | 59216037 A | * | 12/1984 | ............... | 73/82 |

OTHER PUBLICATIONS

J. Von Stebut et al., "Acoustic emission monitoring of single cracking events and associated damage mechanism analysis in indentation and scratch testing", Surface and Coating Technology, Elsevier Science S.A., vol. 116, Sep. 14, 1998, XP002480058, pp. 160-171.

(Continued)

*Primary Examiner* — Thomas P Noland
(74) *Attorney, Agent, or Firm* — Young & Thompson

(57) ABSTRACT

A method for analyzing a scratch from a scratch test includes (a) locating the beginning of the scratch relative to a reference position, (b) making the scratch on a bulk with an indenter while recording the applied force and at least one measurement parameter, as a function of the displacement of the indenter relative to the reference position, (c) acquiring and recording images of the scratch relative to the reference position, (d) synchronizing the recorded images, the applied force and the measurement parameter, as a function of the displacement of the indenter, (e) displaying curves of the applied force and of the measurement parameter as a function of the displacement of the indenter, and (f) displaying in a synchronized way an image of the scratch reconstructed from the recorded images.

14 Claims, 4 Drawing Sheets

OTHER PUBLICATIONS

J. Von Stebut, "Multi-mode scratch testing—a European standards, measurements and testing study", Surface & Coating Technology, Oct. 1, 2005, vol. 200, No. 1-4, XP005063527, pp. 346-350.

J. Stallard et al., "The study of the adhesion of a TiN coating on steel and titanium alloy substrates using a multi-mode scratch tester", Tribology International, vol. 39, No. 2, Feb. 2006, XP005170306, pp. 156-166.

European Search Report dated May 14, 2008, from corresponding European application, in French.

* cited by examiner

METHOD FOR ANALYZING A SCRATCH TEST

TECHNICAL FIELD

The present invention relates to the field of depositing layers on a bulk. More particularly it concerns a method for analyzing a scratch, carried out within the scope of a scratch test.

STATE OF THE ART

When one (or more) coatings are deposited on a bulk (or substrate), it is fundamental to be able to evaluate its adhesion to the bulk, its cohesion as well as elasto-plastic characteristics of the coating/bulk combination. A test known as a scratch test is very commonly used, which is a good means for evaluating these properties.

The principle of the scratch test is to make a scratch under a controlled force and velocity with recording of the parameters of the measurement, with an indenter comprising, for example, a calibrated Rockwell C 200 µm tip, the tip being in diamond or in any other hard material of the same kind. The most commonly measured parameters are the normal force, the tangential force, the penetration depth, the acoustic emission . . . . The fact of specifically controlling the force and the rate of the scratch provides a reproducible and reliable evaluation of the quality of the coating deposit. This method is widely used and is the subject of several standards (ISO, IEN, ASTM . . . ).

Figure 1:
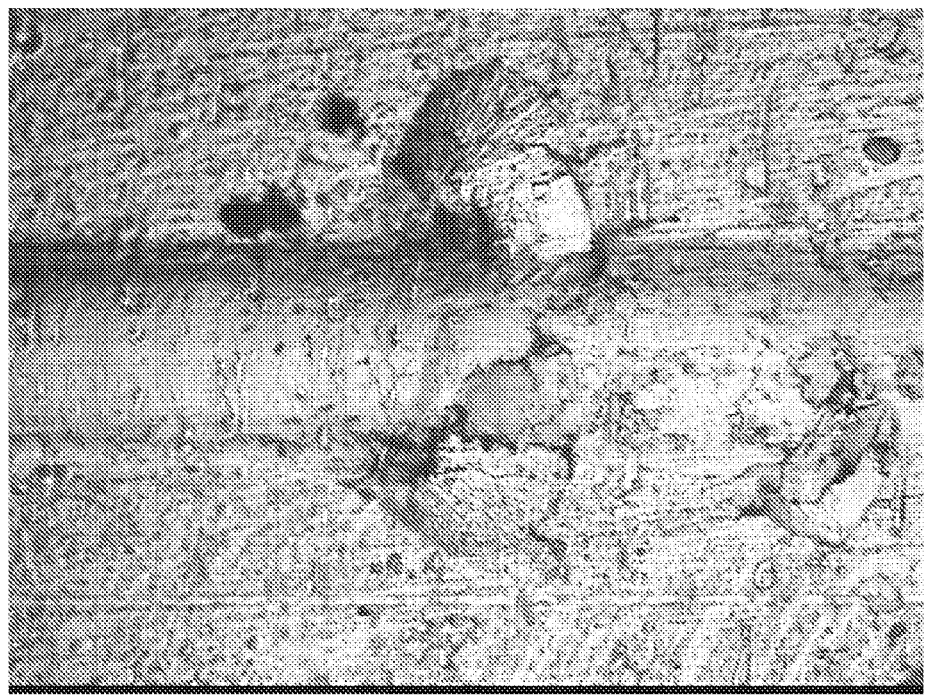

Once the scratch is made, determination of the adhesion and cohesion properties of the coating is carried out by an inspection of the scratch under a microscope and by defining critical loads, i.e. the applied force, corresponding to events which occur at the level of the coating and are clearly identified visually. As an example, FIG. 1 illustrates flaking undergone by a coating, defining brittleness which appears at a given critical load.

The process of a scratch test according to the state of the art is carried out as follows:
- aiming at the starting area of the scratch under a microscope or randomly,
- making the scratch with the indenter,
- synchronized return to the starting area under the microscope for visually inspecting the scratch and for determining the critical loads, and
- passing to the next measurement.

Figure 2:
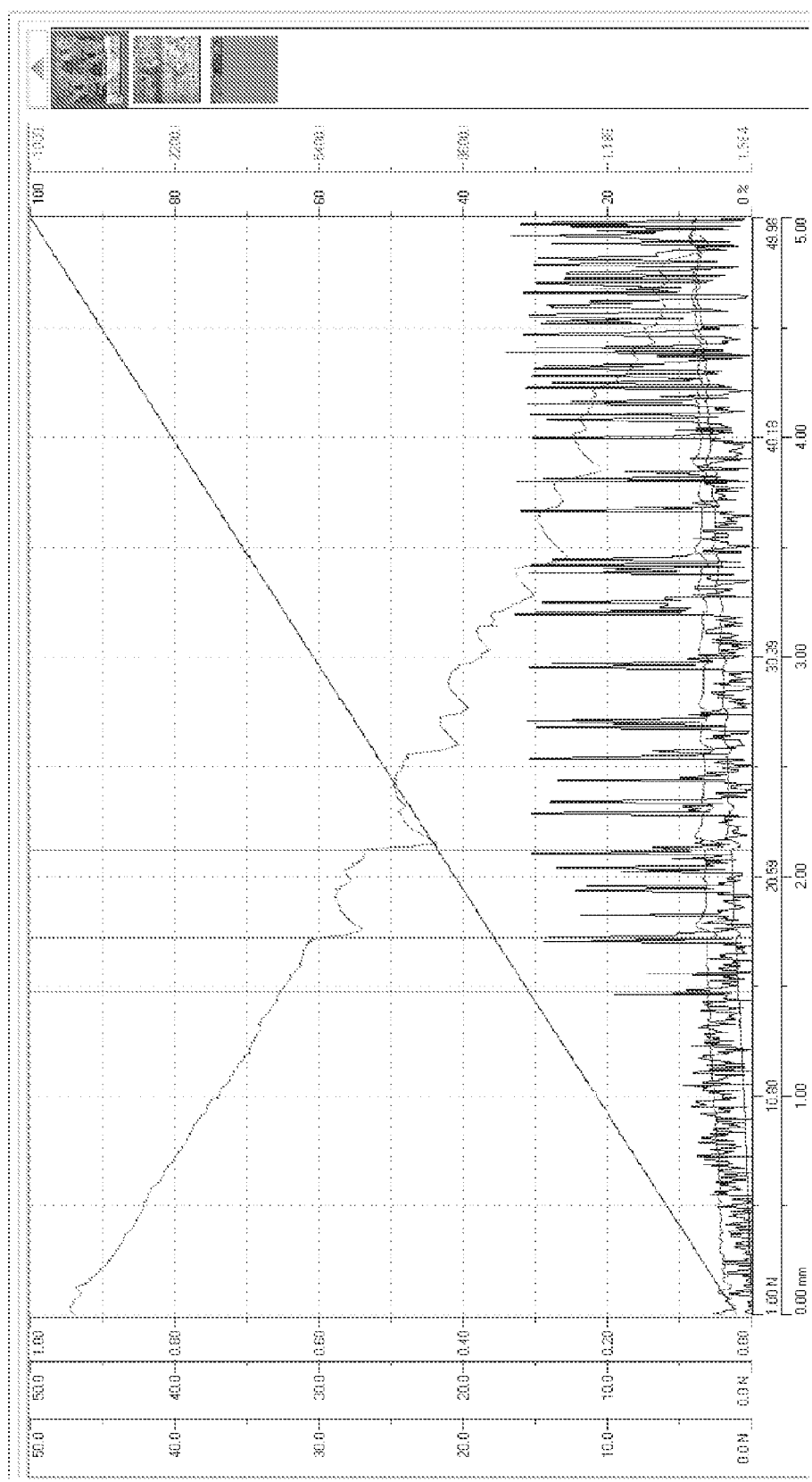

Possibly, a recording of the images corresponding to the critical loads at which a particular event is detected, is carried out. FIG. 2 shows a screen capture illustrating the analysis of a scratch acquired according to the method above. Curves of several parameters may be seen depending on the displacement of the indenter. On a second screen, a few images of the scratch are displayed generally, such as that of FIG. 1 for example. As long as the scratch is seen under the microscope, it is possible to have synchronization between the curves and the images and thus a given image may correspond to an abscissa of the curve. On the other hand, when the scratch is no longer under the microscope, only a few images of the scratch recorded during its making are available in the database. It is then impossible for an a posteriori analysis, to be able to associate with certainty one of these images with the corresponding applied force.

It is easily realized that the limit of this such an operating mode is that the determination of the critical loads is made just after the measurement and this definitively and once and for all, as it is not possible to return to the visual inspection after having moved or changed the sample, the physical synchronization between the image of the scratch and the applied force corresponding to a given image being lost.

The object of the present invention is to propose a method with which analysis of the scratches may be facilitated, particularly by providing the possibility of analyzing the images at any moment relatively to the moment when the scratches are made.

DISCLOSURE OF THE INVENTION

The object of the invention is to propose a method for recording, calibrating, and exploiting a panoramic image without any loss of resolution, representing the totality or a large and significant portion of the scratch. In a particularly advantageous way, the panoramic image may be displayed in a synchronized way with the parameters of the scratch, in order to visually analyze this scratch, still without any loss of resolution, even when the latter is no longer present under the microscope. The problem of the irreversibility of the assignments of the critical optical loads is thereby solved.

More particularly, the invention relates to a method as defined in the claims.

SHORT DESCRIPTION OF THE DRAWINGS

Figure 3:
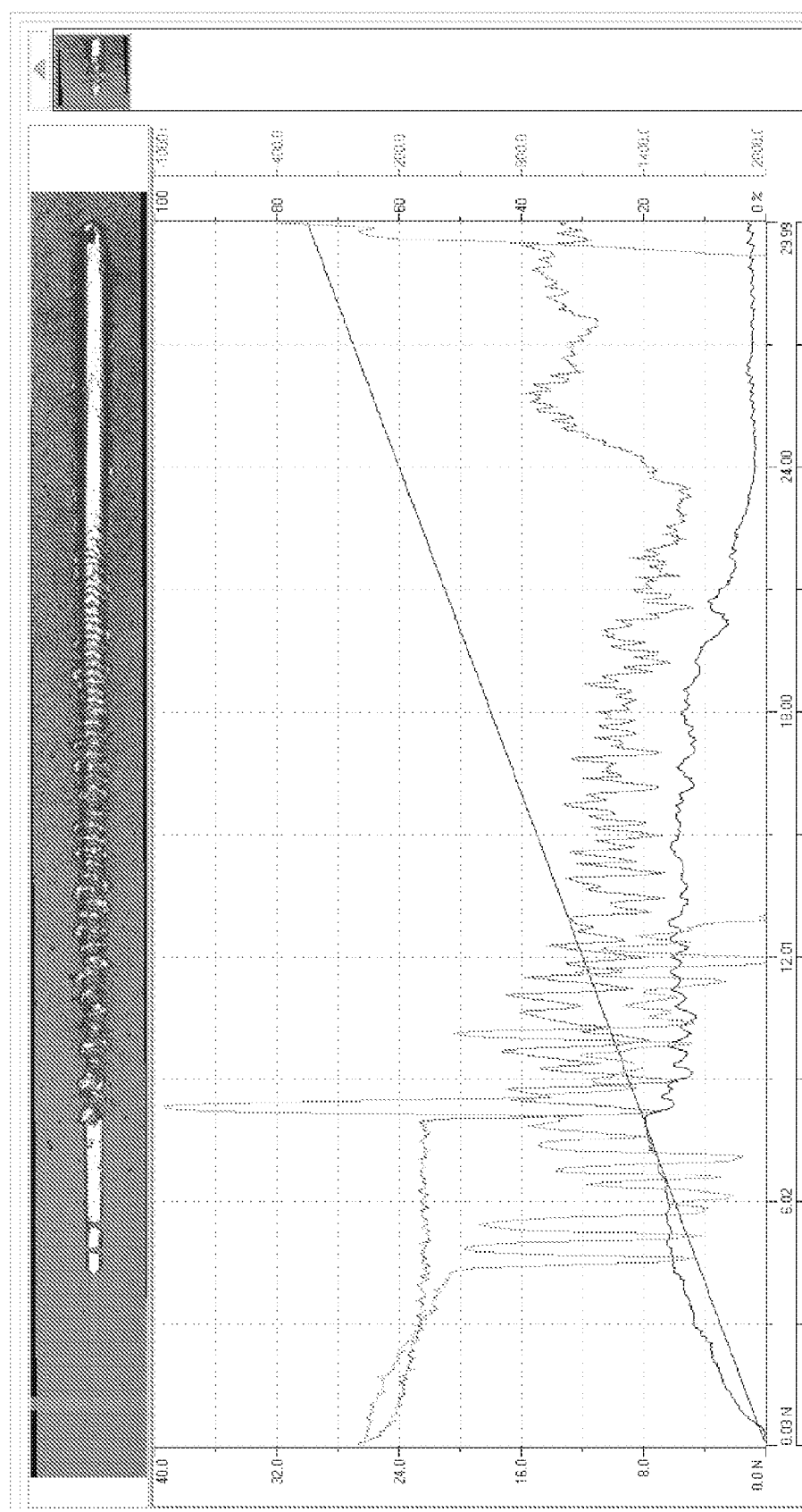
Figure 4:
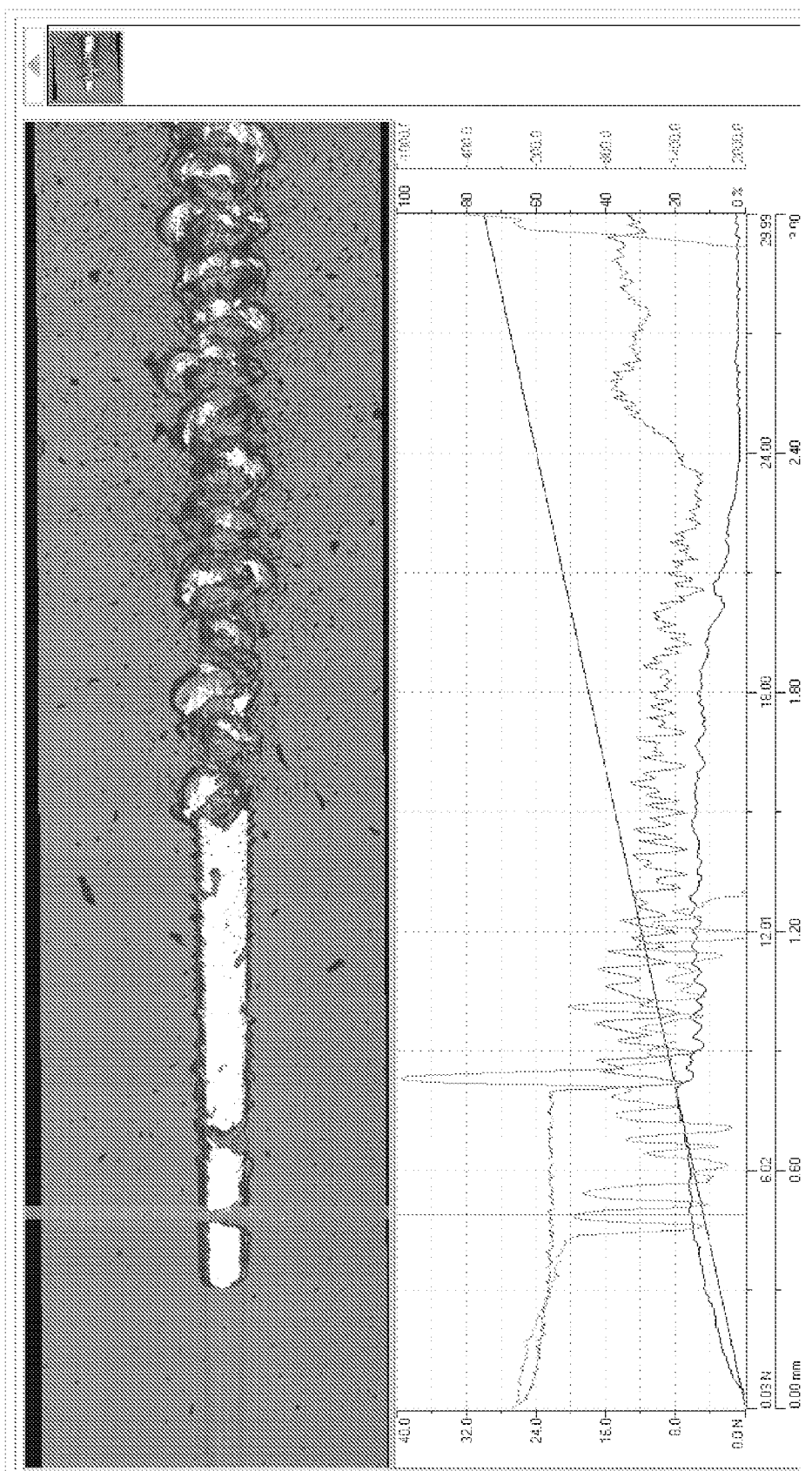

FIGS. 1 and 2 have already been presented above and relate to the state of the art. The description of the present invention which follows is made with reference to the appended drawing, wherein FIGS. 3 and 4 are screen captures illustrating the result to which the method according to the invention may lead.

EMBODIMENT(S) OF THE INVENTION

For applying the invention, a device used in a usual way is provided for carrying out scratch tests and which therefore will not been described in detail. The device notably comprises:
- a digital image acquisition device, provided with at least one objective capable of acquiring highly magnified images, i.e. with magnifications of the microscope kind,
- a support for receiving a bulk to be tested and on which the scratches will be made, and
- an indenter in order to apply a control force on the bulk, so as to make the scratch.

The digital device and the indenter are able to be displaced relatively to the bulk. To do this, the bulk is generally positioned on a mobile table, which may be displaced with high accuracy. It is possible to displace the indenter and the digital device.

Various sensors are also positioned in order to carry out the analysis of the scratch and to detect parameters such as the normal force, the tangential force, the penetration depth, the acoustic emission . . . .

A computer is connected to these various components and applies a program capable of controlling them, of receiving and processing the data provided by the sensors and of displaying on a screen the relevant information for an analysis of the scratch.

In order to achieve the goal sought after by the invention, one of the fundamental aspects of the method for analyzing the scratch lies in the synchronization of an image, a so-called panorama image, of the whole of the scratch, or at least of its significant portion, with curves of the measurement parameters versus the displacement of the indenter. More specifically, as shown in FIGS. 3 and 4, with the synchronization, it is possible to match a portion of the image of the scratch with an abscissa of the curves. The abscissa of the curves represents the distance covered by the indenter. With this synchronization, a force applied to the bulk may be associated with various measurement parameters and with the portion of the matching panorama image.

In the state of the art, this synchronization is performed by the operator who analyzes the curves and visually associates an event identified on the curves with a portion of the scratch which he/she views with the microscope. According to the invention, the parameters of the scratch on the one hand and the panorama image of the scratch on the other hand, are recorded and may be displayed at any moment, while retaining the synchronization.

We shall now detail the steps of a method according to the invention, with reference to a device in which the bulk is positioned on a mobile table.

In a first phase, particularly for obtaining the sought synchronization, various calibrations are carried out. Thus, the distance between the indenter and the image acquisition device is calibrated in order to make known their respective position, for a given position of the mobile table. One also proceeds with calibrating the digital image acquisition device, during which the size of a pixel is determined. In other words, a correspondence is established between a pixel of the digital device and the actual dimension of the point which it represents, at the bulk level. The field of the device is also determined, so that the actual length of a scratch portion located on a single image may be known. It will be recalled that the field is the space (or the surface, in a plane) which the device may sense. The distance between the closest point and the farthest point where the image still has sufficient sharpness is called the field depth.

Before proceeding with making the scratch, the bulk is displaced under the image acquisition device so that the position P0 corresponding to the beginning of the scratch is aimed at by the objective. In this example, it is this position P0 which is used as reference. Adjustment of the focusing of the objective is carried out manually or automatically in order to have a sharp image. The optimum initial distance d0 between the bulk and the objective is thereby determined so that an optimum quality image may be obtained in P0.

A step for measuring and recording the altitude hi of the bulk is then carried out in the area where the scratch will be made. This step is carried out by having this area move past the indenter, with a very low non-destructive load. The topography of the bulk is obtained relatively to the reference position P0, before making the scratch.

The bulk is then displaced so that the position P0 determined as being the beginning of the scratch is positioned under the indenter. The scratch is then made, over a determined length, by applying a force which varies in also a determined way. The parameters of the scratch are measured by means of sensors and recorded.

The image of the scratch is then acquired by the digital device. It will be noted that depending on the respective positioning of the indenter and of the image acquisition device, this operation may be performed quasi simultaneously with the making of the scratch.

The position P0 of the scratch is brought into the sight of the objective of the device. The latter takes and records an image, with the best possible quality. Next, as long as the end of the scratch is not reached, the bulk is displaced by a distance representing a fraction of the field of the objective. With this, images of the whole of the scratch may thereby be collected, without any portion of the latter having not been digitized. Typically, between two consecutive images, the bulk is displaced by a distance corresponding to a half-field.

In order to acquire an image of optimum quality, the topography of the bulk as determined previously, is used for adjusting the position of the bulk relatively to the objective, during acquisition of the images. More particularly, the bulk is placed, along the vertical axis of the table at a distance d of the objective, d being defined as follows:

$$d=d0+hi+pi$$

wherein d0 is the optimum initial distance between the bulk and the objective, as determined previously, hi is the altitude of the bulk in a given position, as determined above pi is the depth of the scratch in a given position, defined by the position of the indenter in the vertical axis.

Advantageously, always with the purpose of obtaining images of optimum quality, for a given position of the scratch, the image acquisition device is controlled in order to take a series of images, at variable distances between the bulk and the objective. As long as d>d0+hi, the device acquires images, the distance between the bulk and the objective varying between two shots, according to a pitch determined as a function of the field depth of the device. Typically, the pitch is of a half-field depth. Next, for a given position with reference to the scratch, each recorded image at a different distance from the bulk undergoes an optimization process, during which a sharp image of the luminance plane is calculated by local DCT (Discrete cosine transform) and by local gradient. A mapping of altitude may thereby be constructed by selecting for each pixel, the altitude of the sharp image where it has a maximum value. After median filtering of the altitude mapping, it is possible to reconstruct the final image.

The central portion of each thereby optimized image is then repositioned by intercorrelation with the central portion of the previous image. With this calculation, the calibration of the size of the pixel may be refined. The thereby obtained recorded images are added one by one and form the panorama image of the whole scratch or at least of its significant portion. For each image forming the panorama image, its calibration parameters and its position relatively to the reference position P0, are stored in memory.

Thus, the panorama image is reformed from a succession of images, each of them being associated with a distance relatively to the reference position. The image/distance association may be stored in memory, so that the panorama image may then be displayed in a synchronized way with the other curves, independently of the physical presence of the bulk.

At the level of the display of the panorama image and of the other curves of the parameters of the scratch, provision may be made, as illustrated in FIG. 3, for positioning on a same screen, a view of the whole of the panorama image and a view of the curves. With a cursor it is possible to specifically indicate the correspondence between the position on the panorama image and the abscissa of the curves associated with this image. For better visibility, provision may also be made as illustrate in FIG. 4, for an enlargement of the panorama image. By means of the performed calibration, this enlargement may be simply accomplished without any loss of synchronization.

It is thereby easy and comfortable to visually analyze the critical loads from the panorama image, corresponding to the curves of the parameters.

It will be noted that for a same measurement, it is further possible to associate several panoramas with different magnifications.

Hence, a method for analyzing a scratch from a scratch test is proposed, with which the curves and the panoramic view of the trace of the scratch may be associated in a same file, in a calibrated and synchronized way, there is no longer any limit to the (either deferred or not) exploitation of the scratch test. Carrying out automated quality control tests may also be contemplated for coatings deposited on bulks.

What is claimed is:

1. A method for analyzing a scratch from a scratch test, implementing a digital image acquisition device provided with a high magnification objective able to shoot only a part of the scratch, a bulk and an indenter for applying a force on the bulk, said method comprising the following steps:

determining the position of the beginning of the scratch relatively to a reference position, making the scratch on the bulk by means of the indenter by recording the applied force and at least one measurement parameter, as a function of the displacement of the indenter on the bulk relatively to the reference position, acquiring and recording a set of images of the whole of the significant portion of the scratch, each image corresponding to a magnified zone of the scratch, the position on the scratch of each recorded images being determined relatively to the reference position, synchronization of the recorded images, of the applied force and of the measurement parameter, as a function of the displacement of the indenter, and displaying the curves of the applied force and of the measurement parameter as a function of the displacement of the indenter, and displaying in a synchronized way with the applied force and with the measurement parameter a panoramic image of the significant portion of the scratch, reconstructed from the recorded images.

2. The method according to claim 1, wherein it begins with a calibration step comprising a step for determining the size of a pixel, with which a correspondence between a pixel of the digital image acquisition device and its corresponding actual dimension at the bulk may be established.

3. The method according to claim 2, wherein the calibration step also comprises a step for determining the field of the image acquisition device.

4. The method according to claim 3, wherein after each shot, the objective and the scratch are displaced with reference to each other, by a fraction of the field of said image acquisition device, two consecutive images being positioned with reference to each other by intercorrelation.

5. The method according to claim 2, wherein the image acquisition device comprises several objectives, the calibration step being applied to each of the objectives.

6. The method according to claim 1, wherein it comprises, consecutively to the step for determining the position of the beginning of the scratch and before making the scratch, a step for measuring and recording the altitude of the bulk carried out by moving the image acquisition device with reference to the area of the bulk where the scratch will be made.

7. The method according to claim 6, wherein the recorded altitude of the bulk is used during the step for acquiring images of the scratch in order to optimize the adjustment of the image acquisition device.

8. The method according to claim 7 wherein the acquisition device comprises an objective, wherein during the step for acquiring and recording images, the bulk is placed at a distance d of the objective, d being defined as follows: $d = d0 + hi + pi$ wherein d0 is the optimum initial distance between the bulk and the objective, hi is the altitude of the bulk in a given position, and pi is the depth of the scratch in a given position, defined by the vertical position of the indenter.

9. The method according to claim 8, wherein, for a given position of the scratch, said device is controlled in order to take a series of images, at variable distances between the bulk and the objective, as long as $d > d0 + hi$, the images of the series being processed so as to reconstruct a final image of the scratch at said given position.

10. The method according to claim 9, wherein after each shot, the objective and the scratch are displaced with reference to each other, by a fraction of the field of said image acquisition device, two consecutive images being positioned with reference to each other by intercorrelation.

11. The method according to claim 8, wherein after each shot, the objective and the scratch are displaced with reference to each other, by a fraction of the field of said image acquisition device, two consecutive images being positioned with reference to each other by intercorrelation.

12. The method according to claim 7, wherein after each shot, the objective and the scratch are displaced with reference to each other, by a fraction of the field of said image acquisition device, two consecutive images being positioned with reference to each other by intercorrelation.

13. The method according to claim 6, wherein after each shot, the objective and the scratch are displaced with reference to each other, by a fraction of the field of said image acquisition device, two consecutive images being positioned with reference to each other by intercorrelation.

14. The method according to claim 1, wherein the reference position is the beginning of the scratch.

* * * * *